United States Patent
Zhang et al.

(10) Patent No.: US 9,656,951 B2
(45) Date of Patent: May 23, 2017

(54) POLYMORPHS OF CDDO ETHYL ESTER AND USES THEREOF

(71) Applicants: Applied Pharmaceutical Science, Inc.; Zhijian Wang, Beijing (CN); Xiaohong Zhang, Beijing (CN)

(72) Inventors: Xiaohong Zhang, Beijing (CN); Lu Song, Beijing (CN); Wendong Sun, Beijing (CN); Kaiyang Liu, Beijing (CN); Chunlei Han, Beijing (CN)

(73) Assignee: Applied Pharmaceutical Science, Inc., Beijing (CN)

( * ) Notice: Subject to any disclaimer, the term of this patent is extended or adjusted under 35 U.S.C. 154(b) by 0 days.

(21) Appl. No.: 14/007,925

(22) PCT Filed: Dec. 6, 2012

(86) PCT No.: PCT/CN2012/086045
§ 371 (c)(1),
(2) Date: Sep. 26, 2013

(87) PCT Pub. No.: WO2014/048033
PCT Pub. Date: Apr. 3, 2014

(65) Prior Publication Data
US 2014/0315997 A1    Oct. 23, 2014

(30) Foreign Application Priority Data
Sep. 28, 2012 (WO) ................ PCT/CN2012/082278

(51) Int. Cl.
| | | |
|---|---|---|
| A61K 31/277 | (2006.01) | |
| C07C 255/47 | (2006.01) | |
| A61K 31/56 | (2006.01) | |
| C07J 63/00 | (2006.01) | |
| C07C 253/34 | (2006.01) | |

(52) U.S. Cl.
CPC .......... C07C 255/47 (2013.01); A61K 31/277 (2013.01); A61K 31/56 (2013.01); C07C 253/34 (2013.01); C07J 63/008 (2013.01); C07B 2200/13 (2013.01)

(58) Field of Classification Search
CPC ..... C07J 63/008; C07J 75/00; C07B 2200/13; C07C 253/34; C07C 255/47; A61K 31/277; A61K 31/56
USPC .......................................... 558/429; 514/519
See application file for complete search history.

(56) References Cited

FOREIGN PATENT DOCUMENTS

WO    2009023232    2/2009

OTHER PUBLICATIONS

Dinkova-Kostova, Albena et al., "Extremely Potent Triterpenoid Inducers of the Phase 2 Response: Correlations of Protection Against Oxidant and Inflammatory Stress," "PNAS," Mar. 22, 2005, vol. 102, No. 12, pp. 4584-4589.
Honda, Tadashi, et al., "A Novel Dicyanotriterpenoid, 2-Cyano-3,12-Dioxooleana-1,9(11)-dien-28-onitrile, Active at Picomolar Concentrations for Inhibition of Nitric Oxide Production, Biorganic & Medicinal Chemistry Letters" 12 (2002), pp. 1027-1030.
Yates, Melinda S., et al., "Pharmacodynamic Characterization of Chemopreventive Triterpenoids as Exceptionally Potent Inducers of Nrf2-regulated Genes," "Molecular Cancer Therapeutics" 2007; 6(1), Jan. 2007.
Bensasson, Rene V., et al., "Potency Ranking of Triterpenoids as Inducers of a Cytoprotective Enzyme and as Inhibitors of a Cellular Inflammatory Response Via Their Electron Affinity and Their Electrophilicity Index," Chemico-Biological Interacts 186 (2010) pp. 118-126.
International Search Report of PCT/CN2012/086045 (part of WO 2014/048033 A1), 2012.
Datta et al., "Crystal Structures of Drugs: Advances in Determination, Prediction and Engineering," www.nature.com/reviews/drugdisc, Jan. 2004, vol. 3, pp. 42-57.
Chemburkar et al., "Dealing with the Impact of Ritonavir Polymorphs on the Late Stages of Bulk Drug Process Development," Organic Process Research & Development, 2000, vol. 4, No. 5, pp. 413-417.
Remington et al., "Remington's Pharmaceutical Sciences," Mack Pub. Co., 1990, pp. 1464-1477.
Honda et al., "Synthetic Oleanane and Ursane Triterpenoids with Modified Rings A and C: A Series of Highly Active Inhibitors of Nitric Oxide Production in Mouse Macrophages," J. Med. Chem., 2000, vol. 43, No. 22, pp. 4233-4246.

*Primary Examiner* — Barbara P Badio
(74) *Attorney, Agent, or Firm* — Foley & Lardner LLP

(57) ABSTRACT

The present invention relates to polymorphic forms of the compound of Formula I (i.e., ethyl 2-cyano-3,12-dioxoleana-1,9(11)-dien-28-oate (CDDO ethyl ester)) and methods of using them for treating a variety of disease states such as cancer and condisitons associated with inflammation.

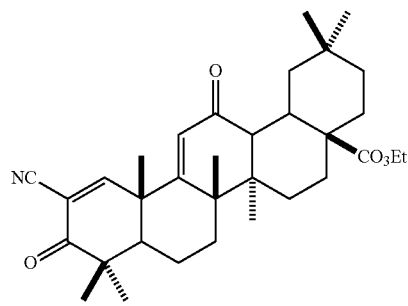

Formula I

38 Claims, 4 Drawing Sheets

Peak List

| Pos. [°2Th.] | Height [cts] | FWHM Left [°2Th.] | d-spacing [Å] | Rel. Int. [%] |
|---|---|---|---|---|
| 7.019370 | 451.248500 | 0.267648 | 12.59346 | 21.17 |
| 9.347051 | 831.295500 | 0.301104 | 9.46191 | 39.00 |
| 10.259280 | 2131.659000 | 0.301104 | 8.62254 | 100.00 |
| 11.961960 | 424.387200 | 0.301104 | 7.39875 | 19.91 |
| 13.124030 | 573.292900 | 0.200736 | 6.74612 | 26.89 |
| 14.124540 | 1773.776000 | 0.267648 | 6.27043 | 83.21 |
| 14.565770 | 1360.492000 | 0.267648 | 6.08146 | 63.82 |
| 15.776800 | 949.847700 | 0.200736 | 5.61727 | 44.56 |
| 16.633660 | 1059.234000 | 0.334560 | 5.32979 | 49.69 |
| 17.648410 | 360.749700 | 0.267648 | 5.02556 | 16.92 |
| 18.996910 | 377.423200 | 0.334560 | 4.67175 | 17.71 |
| 19.592280 | 762.166300 | 0.267648 | 4.53111 | 35.75 |
| 21.037970 | 532.178000 | 0.334560 | 4.22289 | 24.97 |
| 21.702240 | 242.145400 | 0.267648 | 4.09512 | 11.36 |
| 23.436380 | 450.701300 | 0.334560 | 3.79588 | 21.14 |
| 24.172580 | 335.906600 | 0.334560 | 3.68192 | 15.76 |
| 24.970700 | 192.724400 | 0.334560 | 3.56602 | 9.04 |
| 26.557990 | 227.119800 | 0.267648 | 3.35638 | 10.65 |
| 27.236240 | 200.353600 | 0.334560 | 3.27432 | 9.40 |
| 28.079620 | 190.256000 | 0.401472 | 3.17786 | 8.93 |
| 30.357170 | 93.463680 | 0.401472 | 2.94444 | 4.38 |
| 36.777210 | 92.352460 | 0.535296 | 2.44385 | 4.33 |

Figure 1

Peak List

| Pos. [°2Th.] | Height [cts] | FWHM Left [°2Th.] | d-spacing [Å] | Rel. Int. [%] |
|---|---|---|---|---|
| 10.436170 | 758.003500 | 0.200736 | 8.47678 | 16.13 |
| 12.096730 | 1207.613000 | 0.200736 | 7.31662 | 25.70 |
| 13.386570 | 4698.000000 | 0.200736 | 6.61440 | 100.00 |
| 15.426320 | 1453.540000 | 0.200736 | 5.74409 | 30.94 |
| 16.522860 | 185.913200 | 0.401472 | 5.36528 | 3.96 |
| 17.835730 | 1196.765000 | 0.267648 | 4.97320 | 25.47 |
| 18.801090 | 1992.853000 | 0.200736 | 4.71997 | 42.42 |
| 19.585310 | 389.968800 | 0.401472 | 4.53271 | 8.30 |
| 20.935040 | 196.052700 | 0.200736 | 4.24342 | 4.17 |
| 21.389220 | 320.904600 | 0.200736 | 4.15433 | 6.83 |
| 23.677640 | 49.336110 | 0.535296 | 3.75775 | 1.05 |
| 25.387960 | 144.322000 | 0.200736 | 3.50835 | 3.07 |
| 31.928020 | 33.527370 | 0.401472 | 2.80307 | 0.71 |
| 34.189700 | 22.285720 | 0.535296 | 2.62264 | 0.47 |

POLYMORPHS OF CDDO ETHYL ESTER AND USES THEREOF

CROSS-REFERENCE TO RELATED APPLICATION

This application is a national phase application and claims the benefit, under 35 U.S.C. §371, of PCT/CN2012/086045, filed on Dec. 6, 2012, which in turn claims priority to PCT international application No. PCT/CN2012/082278, filed on 28 Sep. 2012, the contents of which are incorporated herein by reference in their entireties.

FIELD OF THE INVENTION

The present invention relates to polymorphic forms of a triterpenoid compound, ethyl 2-cyano-3,12-dioxoleana-1,9(11)-dien-28-oate (CDDO ethyl ester), and methods of using at least one of them in treating a variety of disease states, generally associated with inflammation.

BACKGROUND OF THE INVENTION

Triterpenoids are biosynthesized in plants by the cyclization of squalene. Although being candidates for medicinal use, these naturally occurring molecules display relatively weak biological activity. Accordingly, chemists have sought to synthesize analogues of enhanced potency (Honda et al, 1997 & 1998).

Several synthetic analogs are reported to suppress the denovo formation of cytokine-inducible nitric oxide synthase (iNOS) and cyclooxygenase-2 (COX-2) in macrophages that have been stimulated by IFN-γ or LPS (Suh et al, 1998; Honda et al, 2002). Among them, 2-cyano-3,12-dioxoleana-1,9(11)-dien-28-oate (CDDO), exhibits anti-inflammatory and anti-proliferative activity (Honda et al, 1998 & 2000). As noted, the study of triterpenoids as suppressors of iNOS activity, and specifically in the inhibition of NO production, has demonstrated the high potency of CDDO and CDDO methyl ester ($IC_{50}$<1 nM level). See Honda et al. (2000). However, their therapeutic potential is believed to be not yet fully utilized, even less so for CDDO ethyl ester.

To realize the therapeutic potential of CDDO ethyl ester, depicted in Formula I, the present inventors investigated polymorphic forms of the compound. Consequently, the inventors discovered three polymorphic forms of CDDO ethyl ester, that have such advantageous properties (e.g., better pharmacokinetic profiles and greater systemic exposure) that make them ideal candidates for drug development.

SUMMARY OF THE INVENTION

In one aspect, the present invention provides polymorphs of the compound of Formula I, and/or hydrates or solvates thereof Formula I Among others, these polymorphs include at least two substantially pure crystalline forms and one substantially pure glassy solid form of the compound of Formula I. For convenience, these two crystalline forms are designated herein as Form I and Form II.

In some embodiments, the polymorph is a glassy solid form of the compound of Formula I and characterized having a Tg about 52° C.±10° C.

In some other embodiments, the polymorph is a glassy solid form of the compound of Formula I and characterized by an X-ray powder diffraction pattern having a characteristic peak at diffraction angles 2θ of approximately 14.3°.

In some other embodiments, a glassy solid form of the compound of Formula I is characterized by a purity of ≥85% (i.e., at least 85%). In yet still some embodiments, the purity is at least 95% or 99%.

In still some other embodiments, the polymorph is a crystalline polymorph form I of the compound of Formula I and characterized by an X-ray powder diffraction pattern having characteristic peaks at diffraction angles 2θ of approximately 10.3°, 14.1° and 14.6°.

In still some other embodiments, the polymorph is a crystalline polymorph form I of the compound of Formula I and characterized by the X-ray powder diffraction pattern having characteristic peaks at diffraction angles 2θ of approximately 10.3°, 14.1°, 14.6°, 15.8°, 16.6° and 19.6°.

In still some other embodiments, the polymorph is a crystalline polymorph form I of the compound of Formula I and characterized by the X-ray powder diffraction pattern having characteristic peaks, expressed in terms of the interplanar distance, at 8.6Å, 6.3 Å and 6.1Å.

In still some other embodiments, the polymorph is a crystalline polymorph form I of the compound of Formula I and characterized by the X-ray powder diffraction pattern having characteristic peaks, expressed in terms of the interplanar distance, at 8.6 Å, 6.3Å, 6.1Å, 5.6Å, 5.3Å and 4.5Å.

Another subset of the embodiments of the polymorphs of this invention are of crystalline Form I.

In some of these embodiments, crystalline Form I of the compound of Formula I is characterized by an X-ray powder diffraction pattern having characteristic peaks at diffraction angles 2θ of approximately 10.3°, 14.1°, 14.6°, 15.7°, and 16.6°.

In some other embodiments, crystalline Form I of the compound of Formula I has additional characteristic peaks at diffraction angles 2θ of approximately 9.3° and 19.6°, in its X-ray powder diffraction pattern.

In still some other embodiments, crystalline Form I of the compound of Formula I is characterized by a melting point of 174-177° C.

In some other embodiments, crystalline Form I of the compound of Formula I is characterized by a purity of ≥85% (i.e., at least 85%). In yet still some embodiments, the purity is at least 95% or 99%.

Still another subset of the embodiments of the polymorphs of this invention are of crystalline Form II.

In some of these embodiments, crystalline Form II of the compound of Formula I is characterized by an X-ray powder diffraction pattern having characteristic peaks at diffraction angles 2θ of approximately 10.4°, 12.1° and 13.4°.

In some other embodiments, crystalline Form II of the compound of Formula I has additional characteristic peaks at diffraction angles 2θ of approximately 15.4°, 17.8° and 18.8°, in its X-ray powder diffraction pattern.

In some other embodiments, crystalline Form II of the compound of Formula I is characterized by the X-ray powder diffraction pattern having characteristic peak, expressed in terms of the interplanar distance, at 8.5Å, 7.3Å and 6.6Å.

In some other embodiments, crystalline Form II of the compound of Formula I has additional characteristic peaks, expressed in terms of the interplanar distance, at 5.7Å, 5.0Å and 4.7Å.

In some other embodiments, crystalline Form II of the compound of Formula I is characterized by a melting point of 209-212° C.

In some other embodiments, crystalline Form II of the compound of Formula I has a purity of not less than 85% (e.g., at least 95% or at least 99%).

In another aspect, the invention also relates to methods for making crystalline polymorphs of the compound of Formula I.

An embodiment of the method includes the steps of slurrying excess amount of the compound in a solvent of $CH_2Cl_2$, ethyl acetate, acetonitrile, ethanol, methanol, heptane, or a mixture thereof, for at least 24 hours, and recovering the resulted crystalline polymorph or a glassy solid form.

In some examples, the resultant crystalline forms can be either Form I or Form II.

In some other examples, the compound of Formula I is slurried in the mixed solvent at the room temperature or at 50° C.

In some other examples, the compound of Formula I is slurried in the solvent for at least 48 hours.

The solvent can be an ethyl acetate/heptane mixture, a ethanol/heptane mixture. For example, the ethyl acetate/heptane mixture can have ethyl acetate and heptane in the ratio of 1:10 (weight by weight or volum by volum).

To give a polymorph of this invention, crystallizing the compound of Formula I from a suitable solvent system comprising at least one solvent can be achieved by methods of spontaneous precipitation (evaporation), cooling, or adding anti-solvent (in which the compound of the present invention has relatively lower solubility), in order to achieve oversaturation in a solvent system. Crystallization also can be achieved by using or not using crystal seeds that is suitable for crystallizing the compound of the present invention.

In some other examples, the compound of Formula I of this invention is dissolved in the solvent heptane at the room temperature, followed by a spontaneous precipitation to obtain the desired crystalline Form I, with the melting point of 174-177° C.

In some other examples, a slurry suspension of excess amount of the compound of Formula I of this invention is stirred in the mixed solvent of ethyl acetat/heptane (1:10 weight by weight or volum by volum ) at the room temperature or 50° C for at least 48 hours, to obtain crystalline Form II, with the melting point of 209-212° C.

In some other examples, a slurry suspension of excess amount of the compound of Formula I of this invention is dissolved in the solvent of dichloromethane at the room temperature or 50° C., followed by evaporation of solvent to give a glassy solid form of the compound of Formula I with a Tg in a range of 52° C.±10° C.

The present invention further provides uses of the polymorphs of the compound of Formula I (including crystalline Forms I and II and the glassy solid form) for treating physical disorders or conditions, particularly those associated with inflammation, or for manufacturing medicament for treating physical disorders or conditions, e.g., those involving acute or chronic oxidative stress and inflammation, particularly those characterized in part by over expression of inducible nitric oxide synthase (iNOS) or inducible cyclooxygenase-(COX-2).

Accordingly, the invention also relates to pharmaceutical compositions or medicaments each comprising at least a therapeutically effective amount of crystalline Form I or Form II or the glassy solid form of the present invention, and a pharmaceutically acceptable excipient, adjuvant or carrier. Optionally, the compositions or medicament can further include at least one additional active ingredient.

The pharmaceutical compositions or medicaments of this invention can be in a form or formulation appropriate for the condition or disease to be treated (e.g., in a tablet or capsule), and can be administered in the manner known in the art, e.g., orally.

The pharmaceutical compositions or medicaments of this invention can include 1-99 wt % (e.g., 1-70 wt %, 10-30 wt %,) of a polymorph of the compound of Formula I (e.g., crystalline Form I, crystalline Form II, or glassy solid form).

All the polymorphs of this invention (including the crystalline forms and the glassy solid form) are substantially or approximately pure. As used herein, the term "substantially pure" or "approximately pure" refers to at least 85 wt % (e.g., at least 95 wt % or at least 99 wt %) of the compound of Formula I exists in a polymorph the present invention, particularly in crystalline Form I or Form II.

The main peaks described in the crystalline and the glassy solid form polymorphs above are reproducible and are within the error limit (the specified value ±0.2).

Figure 1:
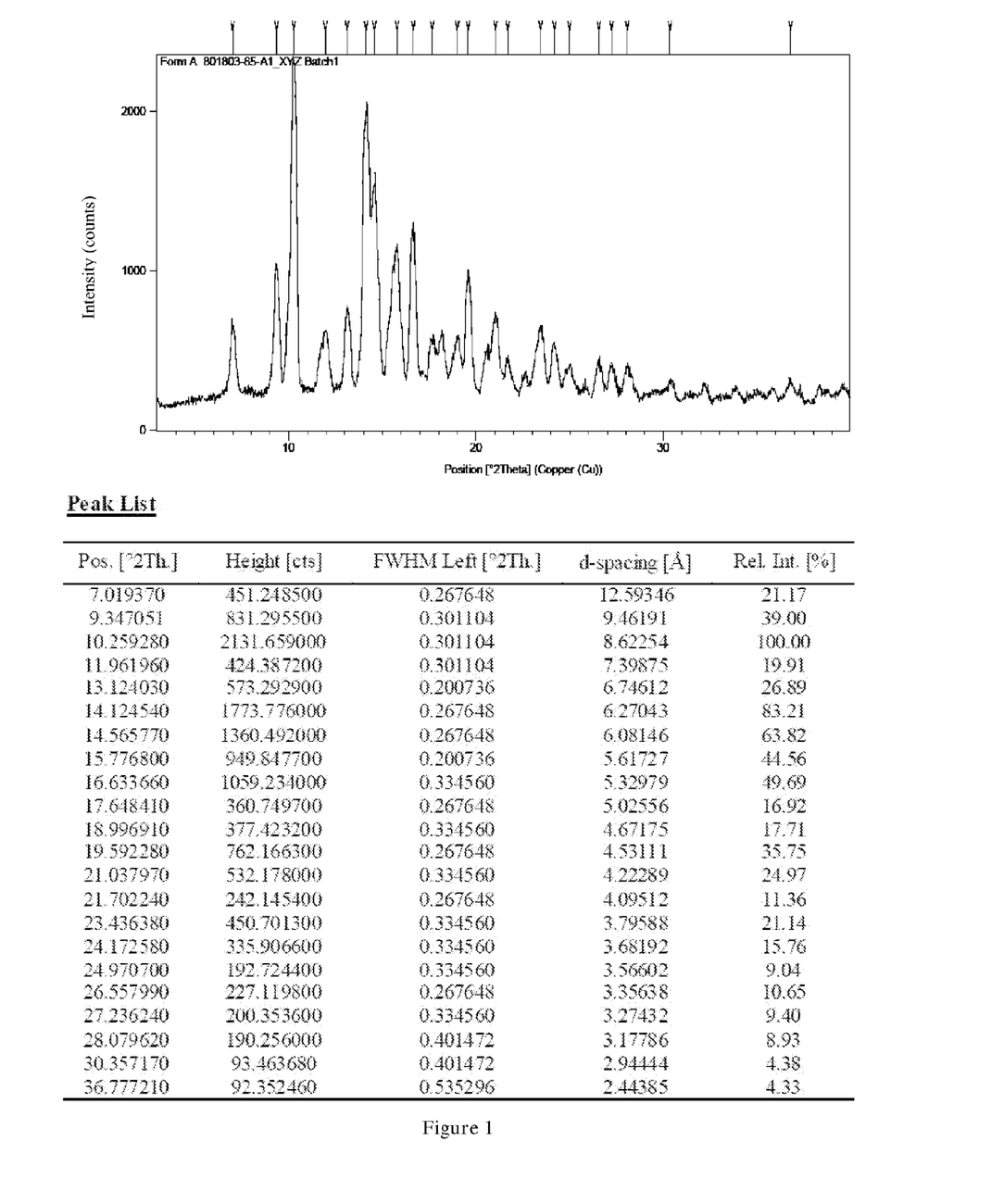
FIG. 1 shows the X-ray powder diffraction pattern of Crystalline Form I of the compound of Formula I

In the present invention, "the X-ray powder diffraction pattern shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 2 refers to the X-ray powder diffraction pattern that show major peaks as in FIG. 2, wherein major peaks refer to those with the relative intensity greater than 10%, preferably greater than 30%, relative to the highest peak (with its relative intensity designated to be 100%) in FIG. 2, respectively.

Also within the scope of this invention are methods for preparing the compound of Formula I each of which includes steps shown in the following scheme:

The present invention also provides the use of the compound of Formula I, or a polymorph or form selected from Crystalline Form I, Crystalline Form II, the glassy solid form, thereof, in manufacturing a medicament for inhibiting IFN-γ-induced NO production in macrophages, or for the treatment of cancer, or for the treatment of a disease, disorder, or condition with an inflammatory component, such as lupus or rheumatoid arthritis, Crohn's disease or ulcerative colitis, a cardiovascular disease, diabetes, one or more complications associated with diabetes wherein the complications are selected from the group consisting of obesity, hypertension, atherosclerosis, coronary heart disease, stroke, peripheral vascular disease, hypertension, nephropathy, neuropathy, myonecrosis, retinopathy and metabolic syndrome (syndrome X), or a combination of two or more thereof.

As used herein, the term "therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount'" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy (i.e., having at least another active ingredient in addition to a polymorph of this invention), the term "therapeutically effective amount" refers to the total amount of the combination objects for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition of the present invention can be produced by the conventional methods in the pharmaceutical field. For example, the active ingredient can be mixed with one or more excipients, then to make the desired formulation. The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc; a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. Preferably, the excipient is suitable for desired formulation and administration type.

As used herein, the term "solvate" refers to the chemical entity formed by the interaction of a solvent and a compound. Suitable solvates are pharmaceutically acceptable solvates, such as hydrates, including monohydrates and hemi-hydrates.

As used herein, the term "active ingredient" is used to indicate a chemical entity which has biological activity. In certain embodiments, an "active agent" is a compound having pharmaceutical utility. For example, an active agent may be an anti-cancer therapeutic.

The term "disease" or "disorder" or "condition" refers to any disease, discomfort, illness, symptoms or indications.

DETAILED DESCRIPTION OF THE INVENTION

Figure 2:
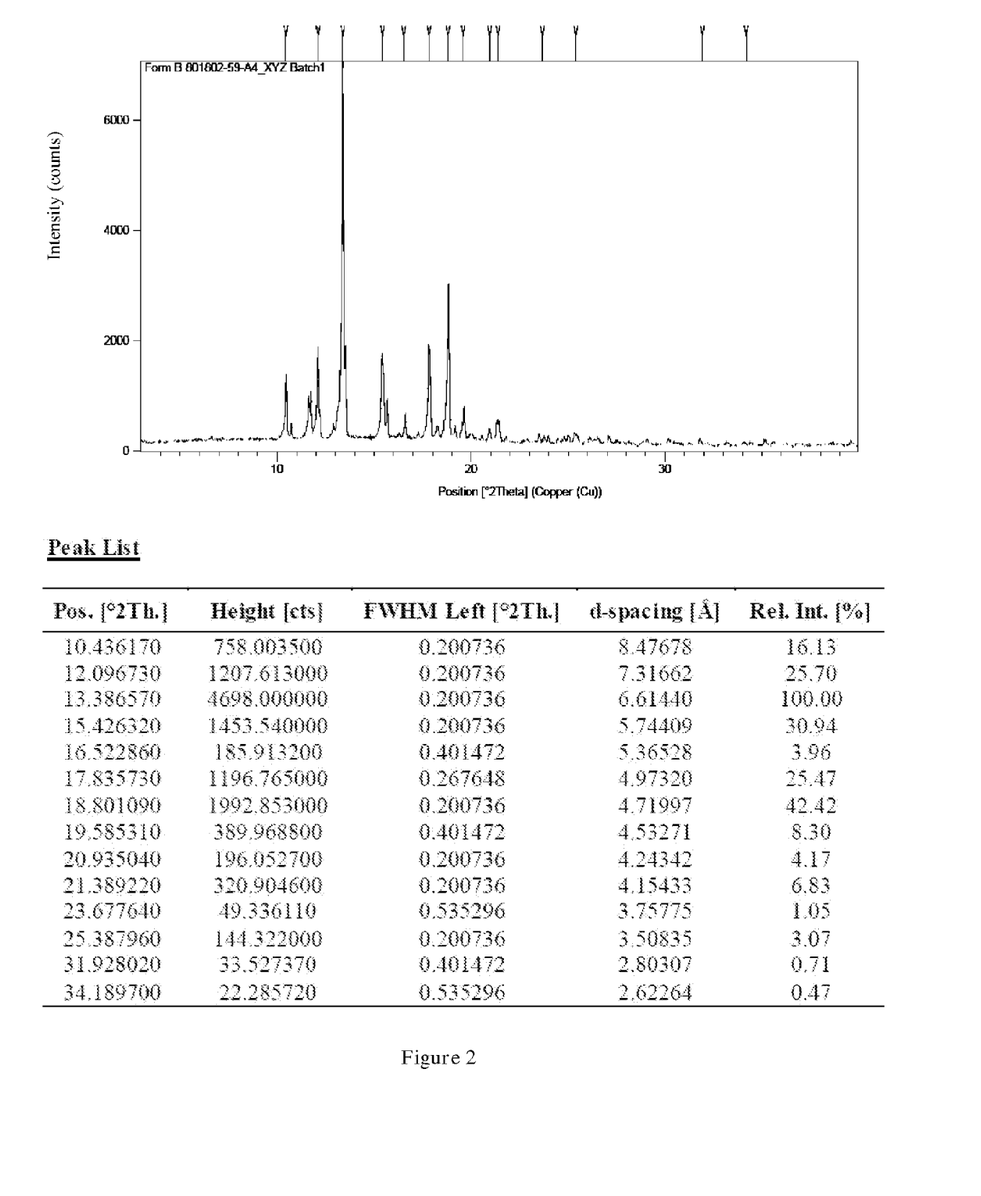
FIG. 2 shows the X-ray powder diffraction pattern of Crystalline Form II of the compound of Formula I
Figure 3:
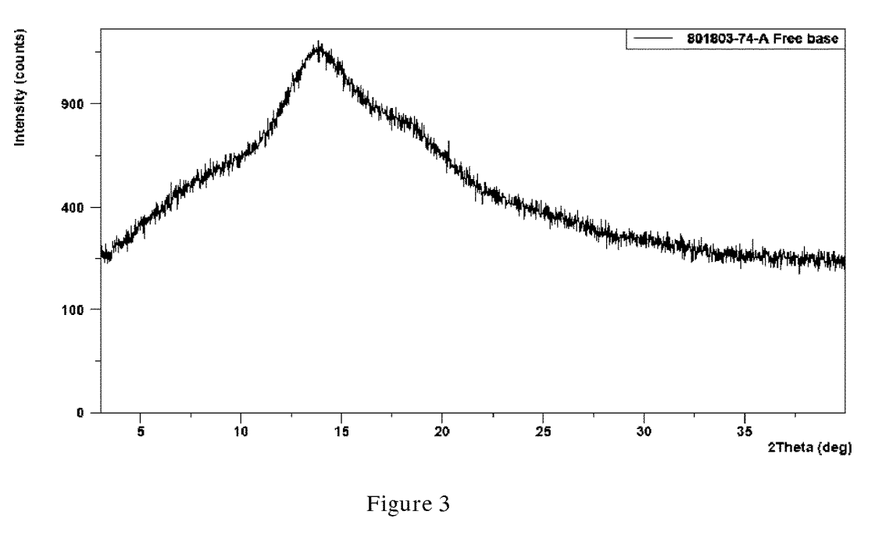
FIG. 3 shows the X-ray powder diffraction pattern of the glassy solid form of the compound of Formula I.

The X-ray powder diffraction (XRPD) patterns shown as in FIGS. 1, 2, 3 were generated on a PANalytical X-ray Diffraction System with Empyrean console. The diffraction peak positions were calibrated by single crystal silicon which has a 2θ value of 28.443 degree. The K-Alpha radiation of an Empyrean Cu LEF X-ray tube was used as the light source of the X-ray.

The present invention is further exemplified, but not limited, by the following examples that illustrate the invention. In the examples of the present invention, the techniques or methods, unless expressly stated otherwise, are conventional techniques or methods known in the art.

EXAMPLE 1

Synthesis of the Compound of Formula I

Step 1 Synthesis of APSN13B-1

| Name | M.W. | Amount | mol | equiv |
|---|---|---|---|---|
| Oleanolic acid | 456 | 1000 g | 2.2 mol | 1 |
| EtI | 156 | 376 g | 2.4 mol | 1.1 |
| $K_2CO_3$ | 138 | 604 g | 4.4 mol | 2 |
| DMF | / | 12 L | / | / |

To a solution of oleanolic acid (1000 g, 2.2 mol) and potassium carbonate (604 g, 4.4 mol) in DMF (12 L) was added ethyl iodide (376 g, 2.4 mol). The mixture was stirred at 45° C. overnight. After disappearance of oleanolic acid detected by HPLC, the mixture was cooled to the room temperature and was poured into water (120 L). The resulting suspension was stirred for 30 minutes. The solid was collected by centrifuge, washed with water (1 L) and dried in vacuo at 50° C. to afford 976 g APSN13B-1 for late ruse. The yield was 92%.

Step 2. Synthesis of APSN13B-2

| Name | M.W. | Amount | mol | equiv |
|---|---|---|---|---|
| APSN13B-1 | 484 | 975 g | 2 mol | 1 |
| $Ac_2O$ | 102 | 612 g | 6 mol | 3 |
| Pyridine | 79 | 474 g | 6 mol | 3 |
| THF | / | 6 L | / | / |
| DMAP | 122 | 24.4 g | 0.2 mol | 0.1 |

To a mixture of APSN13B-1 (975 g, 2 mol), pyridine (474 g), DMAP (24.4 g, 0.2 mol) in THF (6 L) was added acetic anhydride (612 g, 6 mol) at 45° C. The solution was stirred overnight. After the reaction finished, the solution was poured into water (60 L). The solid was collected by centrifuge and dried in vacuo at 45° C. to give 847 g APSN13B-2 for later use. The yield was 80%.

Step 3. Synthesis of APSN13B-3

| Name | M.W. | Amount | mol | equiv |
|---|---|---|---|---|
| APSN13B-2 | 526 | 846 g | 1.6 mol | 1 |
| $H_2O_2$ | 34 | 136 g | 4 mol | 2.5 |
| HCOOH | 46 | 1 L | / | / |
| DCM | / | 5 L | / | / |

To a solution of APSN13B-2 (846 g, 1.6 mol), formic acid (1 L) in DCM (5 L) was added hydrogen peroxide (30%, water solution) (453 g, 4 mol) slowly at room temperature and stirred overnight. The solution was added water (2 L) and extracted with DCM. The organic phase was washed with saturated aqueous $NaHCO_3$ until the water phase was neutral and then washed with brine and dried over anhydrous $NaSO_4$. The organic phase was filtered and the filtrate was evaporated in vacuo to give 871 g APSN13B-3 for a yield of 100%. This material was used for the next reaction without further purification.

Step 4. Synthesis of APSN13B-4

| Name | M.W. | Amount | Mol | equiv |
|---|---|---|---|---|
| APSN13B-3 | 542 | 871 g | 1.6 mol | 1 |
| HBr | 81 | 30 ml | / | / |
| $Br_2$ | 160 | 768 g | 4.8 mol | 3 |
| HAc | / | 7 L | / | / |

To a solution of APSN13B-3 (871 g, 1.6 mol) in acetic acid (5 L) was added a solution of hydrobromic acid (30 ml) in acetic acid (40%) at 45° C. and then was added slowly a solution of bromine (256 g) in acetic acid (700 ml). The mixture was stirred at 45° C. for 30 minutes. Another solution of bromine (512 g) in acetic acid (1.3 L) was added slowly and continued to stir overnight at room temperature. When the reaction finished, the mixture was poured into cold water (35 L). The solid was collected, washed with saturated sodium sulfite solution and dried in vacuo to give the yellow solid 841 g APSN13B-4, for a yield of 97%.

MS-ESI (m/z): 541 $[M+H]^+$

Step 5. Synthesis of APSN13B-5

| Name | M.W. | Amount | mol | equiv |
|---|---|---|---|---|
| APSN13B-4 | 540 | 840 g | 1.56 mol | 1 |
| KOH | 56 | 263 g | 4.7 mol | 3 |
| EtOH | / | 4.5 L | / | / |

A solution of APSN13B-4 (840 g, 1.56 mol) and KOH (263 g, 4.7 mol) in EtOH (4.5 L) was heated under reflux for 30 minutes. After removal of EtOH in vacuo, the resultant mixture was acidified with a 6 N aqueous HCl solution. The aqueous layer was extracted with ethyl acetate (3 L). The organic phase was washed with saturated aqueous $NaHCO_3$, brine and dried over anhydrous $NaSO_4$. The organic phase was filtered and the filtrate was evaporated in vacuo to give 928 g APSN13B-5 for a yield of 100%.

MS-ESI (m/z): 499 $[M+H]^+$.

Step 6. Synthesis of APSN13B-6

| Name | M.W. | Amount | mol | equiv |
|---|---|---|---|---|
| APSN13B-5 | 498 | 927 g | 1.8 mol | 1 |
| Jones reagent | 100 | 400 ml | 1.8 mol | 1 |
| acetone | / | 5 L | / | / |

To a solution of APSN13B-5 (927 g, 1.8 mol) in acetone (5 L) in an ice bath was added Jones reagent (400 ml) dropwise. The mixture was stirred at room temperature until disappearance of APSN13B-5 detected by TLC. After removal of acetone, water was added to the resultant mixture. The aqueous mixture was extracted with DCM. The organic phase was washed with saturated aqueous $NaHCO_3$, brine, dried over anhydrous $NaSO_4$ and filtered. The filtrate was evaporated in vacuo to give crude APSN13B-6. 498 g pure APSN13B-6 was obtained through recrystallization in petroleum and ethyl acetate, for a yield of 54%.

MS-ESI (m/z): 497 $[M+H]^+$

Step 7. Synthesis of APSN13B-7

| Name | M.W. | Amount | mol | equiv |
|---|---|---|---|---|
| APSN13B-6 | 496 | 496 g | 1 mol | 1 |
| $CH_3ONa$ | 54 | 216 g | 4 mol | 4 |
| HCOOEt | 74 | 185 g | 2.5 mol | 2.5 |
| Dry toluene | / | 2 L | / | / |

To a solution of APSN13B-6 (496 g, 1 mol) in dry toluene (2 L) was added ethyl formate (185 g, 2.5 mol) and $CH_3ONa$ (216 g, 4 mol). The mixture was stirred at room temperature for 2 hours. Then the mixture was diluted with ethyl acetate (1 L) and washed with 5% aqueous HCl solution (three times). The water phase was re-extracted with ethyl acetate and the combined organic layers was washed with brine, dried over anhydrous $NaSO_4$ and filtered. The filtrate was evaporated in vacuo to give 497 g APSN13B-7 for a yield of 95%.

MS-ESI (m/z): 525 [M+H]$^+$

| Step 8. Synthesis of APSN13B-8 | | | | |
|---|---|---|---|---|
| Name | M.W. | Amount | mol | equiv |
| APSN13B-7 | 524 | 496 g | 0.94 mol | 1 |
| NH$_2$OH HCl | 69 | 98 g | 1.4 mol | 1.5 |
| EtOH | / | 2.5 L | / | / |
| water | / | 200 ml | / | / |

To a solution of APSN13B-7 (496 g, 0.94 mol) in EtOH (2.5 L) and water (200 ml) was added hydroxylamine hydrochloride (98 g, 1.4 mol). The mixture was heated under reflux for 2 hours. The mixture was concentrated in vacuo and water (2 L) was added. The mixture was extracted with EA (three times). The combined organic layers were washed water and brine, dried over anhydrous $NaSO_4$ and filtered. The filtrate was evaporated in vacuo to give 453 g APSN13B-8 for a yield of 92%.

MS-ESI (m/z): 522 [M+H]$^+$

| Step 9. Synthesis of APSN13B-9 | | | | |
|---|---|---|---|---|
| Name | M.W. | Amount | mol | equiv |
| APSN13B-8 | 521 | 452 g | 0.86 mol | 1 |
| CH$_3$ONa | 54 | 56 g | 1.04 mol | 1.2 |
| EtOH | / | 1.5 L | / | / |

To a solution of APSN13B-8 (452 g, 0.86 mol) in EtOH (1.5 L) in ice bath was added CH$_3$ONa (56 g, 1.04 mol). The mixture was stirred at room temperature for 1 hour. The mixture was concentrated in vacuo and ethyl acetate (2 L) was added. The mixture was washed with 5% aqueous HCl solution (three times). The water phase was re-extracted with EA and the combined organic layers was washed with brine, dried over anhydrous $NaSO_4$ and filtered. The filtrate was evaporated in vacuo to give 429 g APSN13B-9 for a yield of 95%.

MS-ESI (m/z): 522 [M+H]$^+$

| Step 10. Synthesis of APSN13B-10 (Compound of Formula I) | | | | |
|---|---|---|---|---|
| Name | M.W. | Amount | mol | equiv |
| APSN13B-9 | 521 | 428 g | 0.82 mol | 1 |
| DDQ | 227 | 205 g | 0.90 mol | 1.1 |
| tolunene | / | 2.5 L | / | / |

A mixture of APSN13B-9 (428 g, 0.82 mol) and DDQ (205 g, 0.90 mol) in toluene (2.5 L) was heated under reflux overnight. After insoluble was removed by filtration, the filtrate was evaporated in vacuo to give a crude solid. The solid was subjected to flash column chromatography to give 341 g APSN13B-10 for a yield is 80%. The product was further purified through re-crystallization in ethyl acetate and petroleum ether to give chemical purity product. The maximum impurity of final product is less than 0.1%.

MS-ESI (m/z): 520 [M+H]$^+$ $^1$H-NMR (CDCl$_3$): δ8.04 (1H, S), 5.96 (1H, S), 4.17 (2H, t, J=6.9 Hz), 3.05 (1H, d, J=13.5 Hz), 2.95 (1H, d, J=4.5 Hz), 2.04~0.07 (21H, m).

EXAMPLE 2

Preparation of Crystalline Form I of the Compound of Formula I

The compound of Formula I prepared as described above in Example 1 was dissolved in the solvent heptane at the room temperature, followed by a spontaneous precipitation to obtain the desired crystalline Form I, with the melting point of 174-177° C. Its X-ray diffraction pattern depicted in FIG. 1 is summarized in Table 1.

TABLE 1

| 2θ (2 theta) ± 0.2 (degrees) | d-spacing [Å] | Rel. Int. [%] |
|---|---|---|
| 10.3 | 8.6 | 100 |
| 14.1 | 6.3 | 83.2 |
| 14.6 | 6.1 | 63.8 |
| 15.8 | 5.6 | 44.6 |
| 16.6 | 5.3 | 49.7 |
| 19.6 | 4.5 | 35.8 |

EXAMPLE 3

Preparation of Crystalline Form II of the Compound of Formula I

1. A slurry suspension of excess amount of the compound of Formula I prepared from the method described in Example 1 above, was stirred in the mixed solvent of ethyl acetat/heptane (1:10 weight by weight or volum by volum) at the room temperature or 50° C. for at least 48 hours, to obtain crystalline Form II, with the melting point of 209-212° C.

Its X-ray diffraction pattern depicted in FIG 2 is summarized in Table 2.

TABLE 2

| 2θ (2 theta) ± 0.2 (degrees) | d-spacing [Å] | Rel. Int. [%] |
|---|---|---|
| 10.4 | 8.5 | 16.1 |
| 12.1 | 7.3 | 25.7 |
| 13.4 | 6.6 | 100 |
| 15.4 | 5.7 | 30.9 |
| 17.84 | 5.0 | 25.5 |
| 18.8 | 4.7 | 42.4 |

EXAMPLE 4

Preparation of a Glassy Solid Form of the Compound of Formula I

Figure 4:
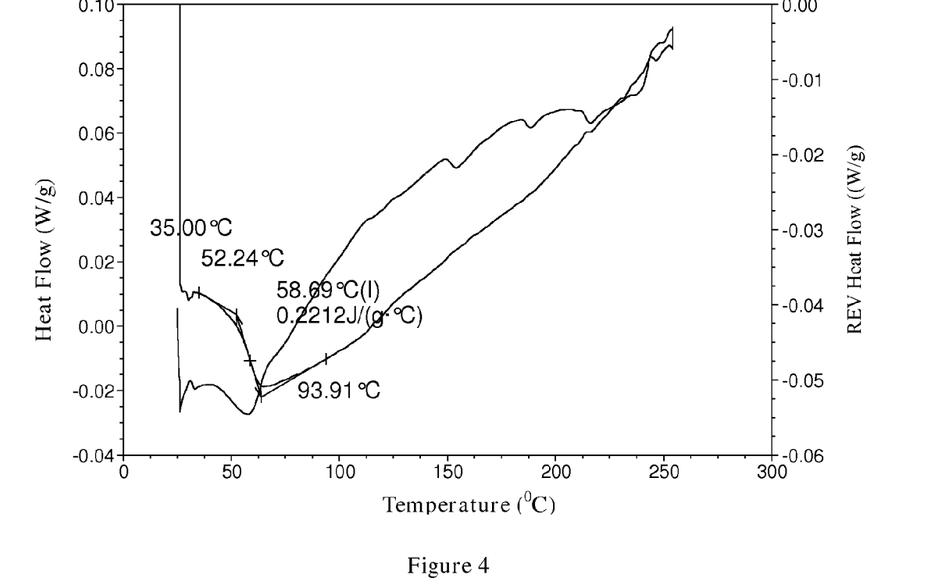
FIG. 4 shows the Heat Flow (w/g) of a glassy solid form.

A slurry suspension of excess amount of the compound of Formula I prepared from the method described in Example 1 above, was dissolved in the solvent of dichloromethane at the room temperature or 50° C., followed by evaporation of solvent to give a glassy solid form of the compound of Formula I with a Tg about 52° C.±10° C. FIG. 3 shows the X-ray powder diffraction pattern of the glassy solid form of the compound of Formula I. FIG. 4 shows the Heat Flow (w/g) of a glassy solid form.

EXAMPLE 5

Preliminary Pharmacokinetics of Polymorphs of the Compound of Formula I

Female CD-I mice were injected ip with 10 mg/kg of the three polymorphs of the compound of Formula I (CDDO ethyl) and methyl 2-cyano-3,12-dioxoIeana-1,9(11)-dien-28-oate (CDDO methyl) in DMSO-cremphor-PBS (1:1:8 weight by weight or volum by volum). Blood samples were collected at 0.083, 0.25, 0.5, 1, 2, 4, 8, and 24 hr post-dose. The levels were quantified by HPLC/MS using compound add to control blood for standard. PK results are shown at Table 3. The systemic exposure of the three polymorphs of the compound of Formula I of CDDO ethyl is higher than that of CDD) methyl. Following is the order: The glassy solid form of CDDO ethyl>Crystalline Form II of CDDO ethyl>Crystalline Form I of CDDO ethyl>CDDO Methyl

TABLE 3

| Compound | $t_{1/2}$ (hr) | $t_{max}$ (hr) | $C_{max}$ (ng/mL) | $AUC_{last}$ (hr*ng/mL) | $AUC_{Inf}$ (hr*ng/mL) |
|---|---|---|---|---|---|
| CDDO Methyl Ester | 6.6 | 0.8 | 363 | 1805 | 1966 |
| The glassy solid form of CDDO ethyl | 16.1 | 0.8 | 513 | 4721 | 7526 |
| Crystalline Form I of CDDO ethyl | 8.3 | 0.8 | 466 | 3221 | 3456 |
| Crystalline Form II of CDDO ethyl | 7.3 | 0.8 | 482 | 3443 | 3840 |

EXAMPLE 6

Stability Determination of Crystal Forms

Crystalline Form II of the compound of Formula I, prepared as described in Example 3, was test at 25° C./60% R.H. and 40° C./75% R.H. There was no significant change of XRD of all the samples. Other polymorphs of this invention were used similar in the study. Compared to other polymorphs of this invention, crystalline Form II of the compound of Formula I was demonstrated to be the most thermodynamically stable crystal form in this study.

EXAMPLE 7

Stability Determination of a Glassy Solid Form

The glassy solid Form of the compound of Formula I, prepared as described in Example 4, was test at 25° C./60% R.H. and 40° C./75% R.H for one week. There was no significant change of XRD of all the samples.

EXAMPLE 8

Measurement of NO in RAW 264.7 Cells Treated with Crystalline Form II of the Compound of Formula I Assay Protocol Procedures
RAW264.7 Cell Culture 1 Maintained RAW264.7 cells in DMEM with 10% FBS at 37° C., 5% $CO_2$.

2. Viewed cultures using a microscope to assess the degree of confluency and confirm the absence of bacterial and fungal contaminants.

3. Removed spent medium.

4. Washed the cell monolayer with pre-warmed D-PBS.

5. With a pipette, moved 3 ml trypsin/EDTA onto the washed cell monolayer, rotated flask to cover the monolayer with trypsin.

6. Examined the cells using a microscope to ensure that all the cells are detached and floating.

7. Re-suspended the cells in a small volume of fresh serum-containing medium to inactivate the trypsin.

8. Harvested cells by centrifugation, 1000 rpm for 5 minutes at the room temperature.

9. Incubated the cells at 37° C. under 5% $CO_2$.

Induction of NO in RAW264.7 Cells

1. The cells were seeded at $1 \times 10^5$/well onto 96-well cell culture plate.

2. After incubation for 2 hours at 37° C. under 5% $CO_2$, the nonadherent cells were removed by aspiration and freshly prepared complete medium with 10 ng/ml IFN-γ and dilluted compounds was added.

3. Incubated the cells at 37° C. under 5% $CO_2$ for another 48 hours.

Measurement of NO in RAW Cells

1. Centrifuged at 1000 rpm for 5 minutes to collect supernatant medium.

2. Prepared 1 ml of a 100 μM nitrite solution by diluting the provided 0.1 M Nitrite Standard 1:1,000 in the matrix or buffer used for the experimental samples.

3. Prepared Nitrite Standard 100, 50, 25, 12.5, 6.25, 3.13, 1.56 and 0 μM, 50 μl/well.

4. Allowed the Sulfanilamide Solution and NED Solution to equilibrate to room temperature (15-30 minutes).

5. Added 50 μl of each experimental sample to wells in duplicate.

6. Used a multichannel pipettor to dispense 50 μl of the Sulfanilamide Solution to all experimental samples and wells containing the dilution series for the Nitrite Standard.

7. Incubated 5-10 minutes at room temperature, protected from light.

8. Used a multichannel pipettor to dispense 50 μl of the NED Solution to all wells.

9. Incubated at the room temperature for 5-10 minutes, protected from light. A purple/magenta color began to form immediately.

10. Measured absorbance within 30 minutes in a plate reader with a filter between 520 nm and 550 nm.

Figure 5:
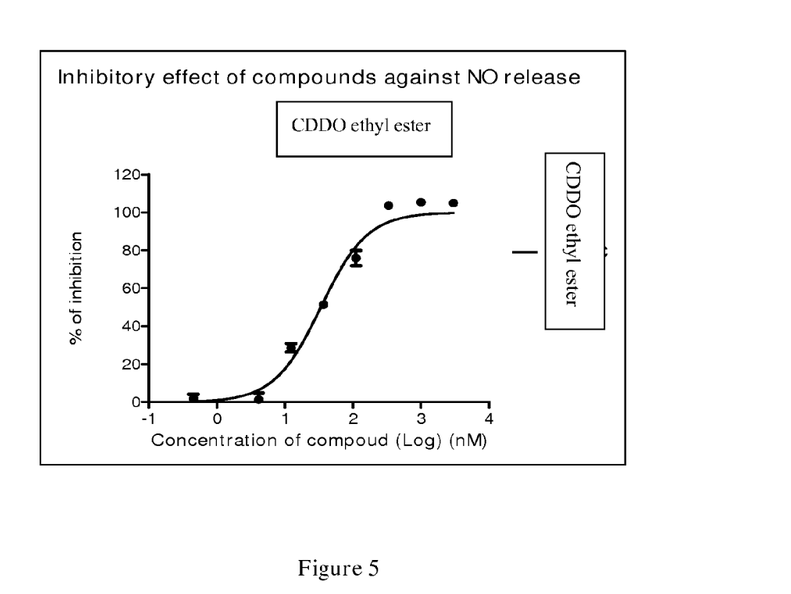
FIG. 5 shows the inhibitory effect of Crystalline Form II of the compound of Formula I (CDDO ethyl ester) against the nitric oxide production induced by IFN-g in mouse macrophages 17.

The inhibitory activities [as measured by the $IC_{50}$ (nM) value] of Crystalline Form II of the compound of Formula I (CDDO ethyl ester) on NO production induced by IFN-g in mouse macrophages 17 are shown in FIG. 5. The $IC_{50}$ of the Crystalline Form II of the compound of Formula I (CDDO ethyl ester) was 34 nM. The $IC_{50}$ of the glassy solid form of the compound of Formula I (CDDO ethyl ester) was 32 nM.

What is claimed is:

1. A polymorph of the compound of Formula I:

Formula I wherein the polymorph is a glassy solid, crystalline Form I, or crystalline Form II; wherein the glassy solid form is characterized by a Tg of about 52° C.±10° C.; wherein the crystalline Form I is characterized by an X-ray powder diffraction pattern having characteristic peaks at diffraction angles 2θ of approximately 10.3°, 14.1° and 14.6°; wherein the crystalline Form II is characterized by an X-ray powder diffraction pattern having characteristic peaks at diffraction angles 2θ of approximately 10.4°, 12.1° and 13.4°.

2. The polymorph of claim 1, wherein the polymorph is a glassy solid form and characterized by a Tg of about 52° C.±10° C.

3. The polymorph of claim 1, wherein the polymorph is of crystalline Form I characterized by an X-ray powder diffraction pattern having characteristic peaks at diffraction angles 2θ of approximately 10.3°, 14.1° and 14.6°.

4. A polymorph of the compound of Formula I:

Formula I wherein the polymorph is of crystalline Form I characterized by an X-ray powder diffraction pattern having characteristic peaks, expressed in terms of the interplanar distance, at 8.6Å, 6.3Å and 6.1Å.

5. The polymorph of claim 1, wherein the polymorph is of crystalline Form I characterized by the X-ray powder diffraction pattern having characteristic peaks at diffraction angles 2θ of approximately 10.3°, 14.1°, 14.6°, 15.8°, 16.6° and 19.6°.

6. The polymorph of claim 4, wherein the polymorph is characterized by an X-ray powder diffraction pattern having characteristic peaks, expressed in terms of the interplanar distance, at 8.6Å, 6.3Å, 6.1Å, 5.6Å, 5.3Å and 4.5Å.

7. The polymorph of claim 1, wherein the polymorph is of crystalline Form I and characterized by an X-ray powder diffraction pattern having characteristic peaks at diffraction angles 2θ of approximately 10.3°, 14.1°, 14.6°, 15.7°, and 16.6°.

8. The polymorph of claim 7, wherein the polymorph has additional characteristic peaks at diffraction angles 2θ of approximately 9.3° and 19.6°.

9. The polymorph of claim 1, wherein the polymorph is of crystalline Form I and characterized by a melting point of 174-177° C.

10. The polymorph of claim 1, wherein the polymorph is a glassy solid form or of crystalline Form I, and is characterized by a purity of ≥85%.

11. The polymorph of claim 10, characterized by a purity of ≥95%.

12. The polymorph of claim 11, characterized by a purity of ≥99%.

13. The polymorph of claim 1, wherein the polymorph is of crystalline Form II and characterized by an X-ray powder diffraction pattern having characteristic peaks at diffraction angles 2θ of approximately 10.4°, 12.1° and 13.4°.

14. The polymorph of claim 13, wherein the X-ray powder diffraction pattern has additional characteristic peaks at diffraction angles 2θ of approximately 15.4°, 17.8° and 18.8°.

15. A polymorph of the compound of Formula I:

Formula I wherein the polymorph is of crystalline Form II characterized by the X-ray powder diffraction pattern having characteristic peak, expressed in terms of the interplanar distance, at 8.5Å, 7.3Å and 6.6Å.

16. The polymorph of claim 15, wherein the X-ray powder diffraction pattern has additional characteristic peaks, expressed in terms of the interplanar distance, at 5.7Å, 5.0Å and 4.7Å.

17. A polymorph of the compound of Formula I:

Formula I wherein the polymorph is of crystalline Form II characterized by a melting point of 209-212° C.

18. The polymorph of claim 13, characterized by a purity of ≥85%.

19. The polymorph of claim 18, characterized by a purity of ≥95%.

20. The polymorph of claim 19, characterized by a purity of ≥99%.

21. A method of preparing a crystalline polymorph of the compound of Formula I, comprising the steps of slurrying excess amount of the compound in a solvent of $CH_2Cl_2$, ethyl acetate, acetonitrile, ethanol, methanol, heptane, or a mixture thereof, for at least 24 hours and recovering the resulted crystalline polymorph or a glassy solid form, Formula I wherein the polymorph is a glassy solid, crystalline Form I, or crystalline Form II; wherein the glassy solid form is characterized by a Tg of about 52° C.±10° C.; wherein the crystalline Form I is characterized by an X-ray powder diffraction pattern having characteristic peaks at diffraction angles 2θ of approximately 10.3°, 14.1° and 14.6°; wherein the crystalline Form II is characterized by an X-ray powder diffraction pattern having characteristic peaks at diffraction angles 2θ of approximately 10.4°, 12.1° and 13.4°.

22. The method of claim 21, wherein the crystalline polymorph of the compound of Formula I is crystalline Form I or Form II.

23. The method of claim 21, wherein the compound of Formula I is slurried in the mixed solved at the room temperature or at 50° C.

24. The method of claim 21, wherein the compound of Formula I is slurried in the solvent for at least 48 hours.

25. The method of claim 21, wherein the solvent is $CH_2Cl_2$, ethyl acetate, acetonitrile, ethanol, methanol, heptane, ethanol/heptane mixture, ethyl acetate/heptane mixture, or a mixture thereof.

26. The method of claim 22, wherein the ethanol/heptane mixture has ethanol and heptane in the ratio of 1:10 weight by weight or volume by volume.

27. A method of preparing a crystalline polymorph of the compound of Formula I, comprising the steps of dissolving the compound in a mixed solvent of ethanol and heptane at the room temperature, spontaneously precipitating the compound into a crystalline polymorph, and recovering the resulted crystalline polymorph, Formula I wherein the polymorph is a glassy solid, crystalline Form I, or crystalline Form II; wherein the glassy solid form is characterized by a Tg of about 52° C.±10° C.; wherein the crystalline Form I is characterized by an X-ray powder diffraction pattern having characteristic peaks at diffraction angles 2θ of approximately 10.3°, 14.1° and 14.6°; wherein the crystalline Form II is characterized by an X-ray powder diffraction pattern having characteristic peaks at diffraction angles 2θ of approximately 10.4°, 12.1° and 13.4°.

28. A method of preparing a glassy solid form of the compound of Formula I, comprising the steps of dissolving the compound in the solvent of dichloromethane at the room temperature or 50° C., followed by evaporation of solvent to give a glassy solid form, Formula I wherein the polymorph is the glassy solid form is characterized by a Tg of about 52° C.±10° C.

29. A pharmaceutical composition comprising a therapeutically effective amount of the polymorph of claim 1, and a pharmaceutically acceptable excipient, adjuvant or carrier.

30. The pharmaceutical composition of claim 29, further comprising an additional active ingredient.

31. The pharmaceutical composition of claim 29, wherein the polymorph is the crystalline Form I or II of the compound of Formula I.

32. The pharmaceutical composition of claim 29, wherein the composition is suitable for oral administration.

33. The pharmaceutical composition of claim 32, wherein the composition is administered in tablet or capsule.

34. The pharmaceutical composition of claim 29, comprising 1-99 wt % of the polymorph.

35. The pharmaceutical composition of claim 34, comprising 1-70 wt % of the polymorph.

36. The pharmaceutical composition of claim 35, comprising 10-30 wt % of the polymorph.

37. A method of reducing or inhibiting nitric oxide production in macrophages in a subject, comprising administering to the subject in need thereof a polymorph of claim 1.

38. A method of preparing the compound of Formula I comprising the steps as shown in the following scheme:

-continued

Formula I wherein the compound of Formula I is a polymorph, and wherein the polymorph is a glassy solid, crystalline Form I, or crystalline Form II; wherein the glassy solid form is characterized by a Tg of about 52° C.±10° C.; wherein the crystalline Form I is characterized by an X-ray powder diffraction pattern having characteristic peaks at diffraction angles 2θ of approximately 10.3°, 14.1° and 14.6°; wherein the crystalline Form II is characterized by an X-ray powder diffraction pattern having characteristic peaks at diffraction angles 2θ of approximately 10.4°, 12.1° and 13.4°.

* * * * *